US009131826B2

United States Patent
Heiligenmann et al.

(10) Patent No.: US 9,131,826 B2
(45) Date of Patent: Sep. 15, 2015

(54) METHOD FOR DISINFECTING CONDUIT SYSTEMS OF A WATER-CONDUCTING APPLIANCE AND SUCH A HOUSEHOLD APPLIANCE

(75) Inventors: Caroline Heiligenmann, Boeblingen (DE); Helmut Jerg, Giengen (DE)

(73) Assignee: BSH Hausgeraete GmbH, Munich (DE)

( * ) Notice: Subject to any disclaimer, the term of this patent is extended or adjusted under 35 U.S.C. 154(b) by 1529 days.

(21) Appl. No.: 12/514,099

(22) PCT Filed: Oct. 30, 2007

(86) PCT No.: PCT/EP2007/061668
§ 371 (c)(1),
(2), (4) Date: May 20, 2009

(87) PCT Pub. No.: WO2008/055811
PCT Pub. Date: May 15, 2008

(65) Prior Publication Data
US 2010/0000577 A1    Jan. 7, 2010

(30) Foreign Application Priority Data

Nov. 9, 2006   (DE) .................. 10 2006 052 890

(51) Int. Cl.
*A47L 15/44*    (2006.01)
*A47L 15/42*    (2006.01)
*A61L 2/20*    (2006.01)

(52) U.S. Cl.
CPC ......... *A47L 15/4227* (2013.01); *A47L 15/4219* (2013.01); *A47L 15/4276* (2013.01); *A61L 2/202* (2013.01); *C02F 2307/12* (2013.01)

(58) Field of Classification Search
None
See application file for complete search history.

(56) References Cited

U.S. PATENT DOCUMENTS

| | | | | |
|---|---|---|---|---|
| 5,960,501 A * | 10/1999 | Burdick | ........................... | 8/158 |
| 6,092,400 A * | 7/2000 | Sumner et al. | .................. | 68/142 |
| 6,506,309 B1 * | 1/2003 | Daniels et al. | ................. | 210/760 |
| 2001/0017145 A1 * | 8/2001 | Rosenbauer et al. | ........... | 134/18 |
| 2007/0251549 A1 | 11/2007 | Heiligenmann et al. | | |

FOREIGN PATENT DOCUMENTS

| | | |
|---|---|---|
| DE | 3232057 A1 | 3/1984 |
| DE | 19513352 A1 | 10/1996 |
| DE | 199916136 A1 | 10/2000 |
| EP | 1088509 A1 | 4/2001 |
| WO | 2005039377 A1 | 5/2005 |

* cited by examiner

Primary Examiner — Michael Kornakov
Assistant Examiner — Ryan Coleman
(74) Attorney, Agent, or Firm — James E. Howard; Andre Pallapies

(57) ABSTRACT

A water-conducting household appliance and a method for disinfecting a conduit system of a water-conducting household appliance. The method feeds a gaseous disinfectant into a liquid circulating in the conduit system. The water-conducting household appliance includes a conduit system for circulating liquid, and a disinfector with a gas injector for injecting a gaseous disinfectant into a liquid circulating in the conduit system.

8 Claims, 1 Drawing Sheet

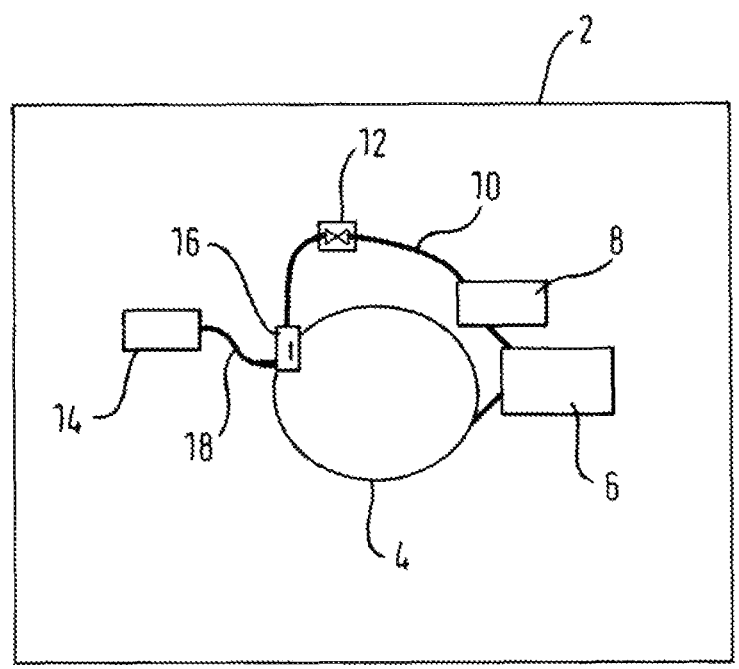

METHOD FOR DISINFECTING CONDUIT SYSTEMS OF A WATER-CONDUCTING APPLIANCE AND SUCH A HOUSEHOLD APPLIANCE

BACKGROUND OF THE INVENTION

The invention relates to a method for the at least sectional disinfection of a water-conducting household appliance as well as to a correspondingly embodied water-conducting household appliance, particularly a dishwasher and a disinfection device.

With water-conducting household appliances such as dishwashers for example, the washing liquor circulated in the dishwasher can become laden to a significant extent with organic contaminants such as food residue etc for example. This food residue is not always completely removed at the end of the rinsing cycle when the washing liquor is pumped away. Food residue remaining can cause unpleasant smells.

BRIEF SUMMARY OF THE INVENTION

The object of the invention is to provide a remedy for this.

This object of the invention is achieved by a method for at least sectional disinfection of a conduit system of a water-conducting household appliance, particularly a dishwasher, in which in a disinfecting step, a gaseous disinfectant is fed into the liquid circulating in the conduit system. In such cases in the case of a dishwasher at the conduit system comprises a pump well arranged in the floor pan of the dishwasher in which washing liquor circulated in the dishwasher collects. By means of a circulation pump the washing liquor collecting in the pump well can be fed via corresponding conduits of the conduit system to spray arms which apply washing liquor to crockery and cutlery to be cleaned. To heat up the washing liquid in such cases a flow-through heater can also be provided. The washing liquor flows from the crockery and cutlery to be cleaned and collects again in the pump well. To achieve an at least sectional disinfection of the conduit system, a gaseous disinfectant is fed into a circulating liquid. The circulating liquid in this case can involve a washing liquor circulated during a cleaning program, or the disinfecting step is executed separately independently of the cleaning program, with in this case water essentially having a gaseous disinfectant added to it. Accordingly the inventive method can be executed as an individual step by default within the framework of a prespecified cleaning program or alternately manually as required by an operator, for example by actuation of a corresponding actuation element on the water-conducting household appliance.

All suitable gaseous disinfectants such as chlorine, chlorine dioxide or hydrogen peroxide can be used to example. Preferably there is provision however for ozone to be used as the disinfectant.

In this case there is provision in a preferred embodiment for the ozone to be generated by means of an ozone generator, and therefore for storage in a corresponding pressurized gas container not to be necessary. Such ozone generators are known and generate the ozone by means of electrical discharges or by means of UV light.

Furthermore there is preferably provision for ozone to be fed under vacuum pressure into the circulating liquid. A venturi nozzle can be used to this purpose for example. Alternately there can also be provision for ozone to be fed into the circulating liquid by being pumped in by a pump.

Basically the gaseous disinfectant can be fed in at any suitable point of a conduit system of a water-conducting household appliance, such as a dishwasher for example. Preferably there is provision however for liquor to be conveyed through a bypass in the disinfecting step and for ozone to be fed in in the bypass.

Furthermore there is preferably provision for liquor to circulate at a reduced rate in the disinfecting step. This can be achieved for example by a circulation pump circulating the washing liquor running at a reduced speed and thus the outflow of washing liquor from spray arms of the conduit system of a dishwasher being reduced. At the same time, however the flow speed is still high enough for sufficient ozone to be sucked in in order to achieve a disinfection of the conduit system.

The invention further relates to a water-conducting household appliance, particularly a dishwasher, with a conduit system in which liquor circulates at least some of the time during operation. The conduit system on a dishwasher in this case can involve a pump well in which washing liquor collects which is conveyed by means of a circulation pump through a flow-through heater and is then subsequently applied by means of spray arms to crockery and cutlery to be cleaned.

The inventive water-conducting household appliance is characterized in that disinfectant features at least one gas introduction medium which is embodied for feeding gaseous disinfectant into a liquid circulating in a conduit system. This makes it possible to trigger a disinfecting process both during the regular operation within the framework of a washing program and alternately at the request of an operator by manual initiation.

All suitable gaseous disinfectants can be used, such as chlorine, chlorine dioxide or hydrogen peroxide. Preferably however there is provision for the disinfectant to feature at least one ozone generator so that ozone can be generated as required for the disinfection and thus corresponding storage by means of a gas tight container is not necessary.

The gas can be fed to example by means of a pump which pumps the gaseous disinfectant into the circulating liquid. Preferably, however, there is provision for the gas introduction medium to be embodied for injection at negative pressure. To this end there is preferably provision for the gas introduction medium to feature a Venturi nozzle so that a negative pressure is built up in the liquid flowing through the Venturi nozzle.

In a preferred embodiment there is provision in this case for the conduit system to feature a central collection area, such as a pump well for example, in which circulating liquid collects. Furthermore a bypass is provided which connects this collection area with the gas introduction medium such as a Venturi nozzle example.

In this case the bypass has a connection to a circulation pump in order to let liquid circulate in the conduit system.

There is also provision for a flow-through heater to be arranged in the bypass. In this case a combination of a circulation pump and an integrated flow-through heater can also be used as an alternative.

In a further embodiment there is provision for a valve to be provided in the bypass. By opening the valve the bypass is released so that liquid can now circulate through the bypass, whereas in normal operation the valve is closed and the bypass blocks.

There is also preferably provision for the pump speed to be controllable. This allows operation of the circulation pump at reduced speed when disinfectant is being fed into the circulating liquid. In this case, for operation with a circulation pump at reduced speed, no water is conducted into the washing area of the dishwasher. However, sufficient ozone is fed at vacuum pressure into the circulating liquid.

BRIEF DESCRIPTION OF THE DRAWINGS

The invention is explained below with reference to a drawing. The figure shows:

FIG. 1 a schematic view of a cross-section through a floor pan of an inventive dishwasher.

DETAILED DESCRIPTION OF EXEMPLARY EMBODIMENTS OF THE PRESENT INVENTION

The figure shows a schematic representation of a floor pan 2 of a dishwasher. Arranged above the floor pan 2 is a washing chamber with a washing area (not shown) in which crockery and cutlery can be arranged in crockery baskets. There are also spray arms in the washing area which wet the crockery and cutlery to be washed with washing liquor.

Provided in the middle of the floor pan 2 is a pump well 4 which is so arranged and is connected to the washing area that further washing liquor running off the crockery and cutlery to be cleaned collects in the pump well 4.

Also arranged in the floor pan 2 are a circulation pump 6, a flow-through heater 8, a valve 12, an ozone generator 14 and a Venturi nozzle 16. A bypass 10 connects the pump well 4, the circulation pump 6, the flow-through heater 8 and the Venturi nozzle 16 such that, when the valve 12 is open, washing liquor can be conducted from the pump well 4 by the circulation pump 6 through the flow-through heater to the Venturi nozzle 16. By further conduit means not shown in the figure washing liquor is then conducted from the Venturi nozzle to the spray arms arranged in the washing area.

The ozone generator 14 is connected by means of a pipe 18 with the Venturi nozzle 16.

If for example a disinfecting process of the conduit system of the dishwasher is to be executed within the framework of a washing program or by manual initiation by an operator, a water switch (not shown) will be closed by a controller and the valve 12 opened so that the bypass 10 lets liquid through. In addition the circulation pump 6 is now operated at a reduced speed and the ozone generator 14 activated. The circulation pump 6 conveys washing liquor out of the pump well 4, via the flow-through heater 8 and the open valve 12 to the Venturi nozzle 16. In this case the speed of the circulation pump 6 is so high that the flow speed of the circulating liquid causes ozone to be fed under negative pressure into the Venturi nozzle 18 in a sufficient quantity. Subsequently the washing liquor provided with ozone flows through a pipe system (not shown) to the spray arms and effects a disinfection there by oxidization.

A disinfection of the washing chamber itself is achieved by ozone coming out of the circulating washing liquor and thus removing dirt and bacteria on the surfaces of the washing chamber. After completion of the disinfecting step the water switch returns to its open position and the valve 12 is closed so that the dishwasher is available again for a normal washing cycle List of Reference Characters:
2 Floor pan
4 Pump well
6 Circulating pump
8 Flow-through heater
10 Bypass
12 Valve
14 Ozone generator
16 Venturi nozzle
18 Feed pipe

The invention claimed is:

1. A water-conducting household appliance, comprising:
a conduit system for circulating liquid;
a disinfector with a gas injector for injecting a gaseous disinfectant into a liquid circulating in the conduit system; and
a selectively operable valve in the conduit system and connected to the disinfector to activate the disinfector, the selectively operable valve being structurally arranged and configured to effect manual initiation of the disinfector by an operator.

2. The water-conducting household appliance of claim 1, wherein the disinfector comprises an ozone generator.

3. The water-conducting household appliance of claim 1, wherein the gas injector comprises a Venturi nozzle.

4. The water-conducting household appliance of claim 1, wherein the conduit system comprises a collection area for the circulating liquid and a bypass that connects the collection area with the gas injector.

5. The water-conducting household appliance of claim 4, further comprising a circulating pump connected to the bypass.

6. The water-conducting household appliance of claim 5, wherein the speed of the circulating pump is controllable.

7. The water-conducting household appliance of claim 4, wherein the bypass comprises a flow-through heater.

8. The water-conducting household appliance of claim 4, wherein the bypass comprises said valve.

\* \* \* \* \*